(12) United States Patent
Veltman et al.

(10) Patent No.: US 9,625,443 B2
(45) Date of Patent: Apr. 18, 2017

(54) RAPID SMALL VOLUME DETECTION OF BLOOD AMMONIA

(71) Applicant: THE BOARD OF TRUSTEES OF THE LELAND STANFORD JUNIOR UNIVERSITY, Palo Alto, CA (US)

(72) Inventors: Thomas Richard Veltman, Towson, MD (US); Chun J. Tsai, Cupertino, CA (US); Matthew William Kanan, Palo Alto, CA (US); Gilbert Chu, Palo Alto, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 150 days.

(21) Appl. No.: 14/619,609

(22) Filed: Feb. 11, 2015

(65) Prior Publication Data

US 2015/0226702 A1     Aug. 13, 2015

Related U.S. Application Data

(60) Provisional application No. 61/938,467, filed on Feb. 11, 2014.

(51) Int. Cl.
*G01N 27/404*     (2006.01)
*G01N 33/49*      (2006.01)
(Continued)

(52) U.S. Cl.
CPC ..... *G01N 33/4925* (2013.01); *G01N 27/4045* (2013.01); *G01N 27/4074* (2013.01); *G01N 33/0054* (2013.01)

(58) Field of Classification Search
CPC .... G01N 27/30; G01N 27/307; G01N 27/304; G01N 27/403; G01N 27/4045; G01N 33/0054
See application file for complete search history.

(56) References Cited

U.S. PATENT DOCUMENTS 4,452,682 A     6/1984   Takata et al.
4,615,340 A  *  10/1986  Cronenberg ......... A61B 5/1405
                                                    204/415
(Continued)

OTHER PUBLICATIONS

PCT International Search Report & Written Opinion for related International Patent Application No. PCT/US2015/015489, mailed May 19, 2015 (10 pages).
(Continued)

*Primary Examiner* — Alex Noguerola
(74) *Attorney, Agent, or Firm* — Merchant & Gould, P.C.

(57) ABSTRACT

A method for measuring ammonia in a blood sample may involve positioning the blood sample in proximity with an ammonia gas sensor, generating a current with the ammonia gas sensor in response to ammonia gas released from the blood sample, and measuring the current generated by the ammonia gas sensor, using a current measurement member coupled with the ammonia gas sensor. A device for measuring an ammonia level in a blood sample may include a blood sample containment member, an ammonia gas sensor coupled with the blood sample containment member, and a current measurement member coupled with the ammonia gas sensor. The method and device may be used to measure an ammonia level in a blood sample as small as one drop of blood, or approximately 0.05 mL of blood.

32 Claims, 3 Drawing Sheets

(51) Int. Cl.
G01N 33/00 (2006.01)
G01N 27/407 (2006.01)

(56) References Cited

U.S. PATENT DOCUMENTS

| | | | |
|---|---|---|---|
| 4,654,197 A | 3/1987 | Lilja et al. | |
| 6,248,224 B1 * | 6/2001 | Kitzelmann | G01N 33/0054 204/414 |
| 7,410,468 B2 * | 8/2008 | Freeman | A61B 5/1411 600/564 |
| 8,323,469 B2 * | 12/2012 | Scarano | A61B 5/14542 204/406 |
| 2004/0253492 A1 | 12/2004 | Vajo | |
| 2005/0252790 A1 | 11/2005 | Dobson et al. | |

OTHER PUBLICATIONS

Proelss et al., "Rapid Determination of Ammonia in a Perchloric Acid Supernate from Blood, by Use of an Ammonia-Specific Electrode," Clinical Chemistry, 1973, pp. 1162-1169, vol. 19 No. 10.
Schaffar et al., "Highly Miniaturized and Integrated Biosensor for Analysis of Whole Blood Samples," Clinical Chemistry, 1999, pp. 1678-1679, vol. 45 No. 9.

* cited by examiner

RAPID SMALL VOLUME DETECTION OF BLOOD AMMONIA

CROSS-REFERENCE TO RELATED APPLICATIONS

This application claims priority to U.S. Provisional Patent Application No. 61/938,467, entitled "Rapid Small Volume Detection of Blood Ammonia," filed on Feb. 11, 2014. The full disclosure of the above-listed patent application is hereby incorporated by reference herein.

BACKGROUND

Hyperammonemia is a metabolic disturbance characterized by excess ammonia in the blood. It is a dangerous condition that may lead to brain dysfunction (encephalopathy) and even death. Some cases of sudden infant death syndrome (SIDS) have been linked to undiagnosed metabolic disorders that caused hyperammonemia. A number of different conditions may cause hyperammonemia, such as inherited genetic mutations, liver damage, blind loop syndrome associated with gastrointestinal surgery, inflammatory bowel disease and some types of chemotherapy medications used for cancer treatment. Hyperammonemia is typically simple to treat if detected early enough. Unfortunately, there are no currently available, simple, quick tests for detecting hyperammonemia. This means that many cases of hyperammonemia go undetected until it is too late, often resulting in patient death.

Conditions that cause hyperammonemia may be inherited or acquired. Many different inherited genetic mutations may cause hyperammonemia. Ammonia is converted to the less toxic substance urea prior to excretion in urine by the kidneys. Some children have genetic mutations that disrupt the urea cycle in the body. These children require lifetime monitoring of blood ammonia levels. Acquired causes of hyperammonemia, including those mentioned above, also require long term monitoring of blood ammonia levels. Unfortunately, there is no convenient way for patients to monitor their blood ammonia levels on an ongoing basis.

Sudden infant death syndrome is the largest single cause of death in children in the industrialized world. A small but significant fraction of SIDS deaths are due to an unrecognized metabolic disorder associated with hyperammonemia. Many of these disorders become symptomatic either in the newborn or in the first few months of life. Indeed, some states perform neonatal tests for genetic diseases, such as fatty acid oxidation disorders or organic acidemias, which are associated with hyperammonemia. Rather than measuring blood ammonia levels directly, the tests employ tandem mass spectrometry to detect specific metabolites that accumulate in these conditions. The tests must be performed from a drop of blood obtained by a heel stick of the newborn infant, because venipuncture is technically difficult, morbid, and invasive. Currently, the United States screens for only a small number of hyperammonemia-associated defects. Other economically advanced countries offer few screening tests of any kind.

Although hyperammonemia damages the brain, it can be effectively and simply treated if detected early enough. One simple treatment involves administering lactulose to the patient. Lactulose is a non-absorbed sugar, which acidifies the stool and thus prevents absorption of ammonia into the blood from the intestine. Another treatment involves administering the antibiotic Rifaxamin, which kills urea-producing bacteria in the intestine. These treatments are simple, inexpensive and effective, if used early enough in the course of hyperammonemia.

The most pressing issue in detecting and treating hyperammonemia lies in detection. All of the currently available detection methods require processing blood to acquire plasma, and then testing the plasma for ammonia. Processing involves spinning the blood in a centrifuge to separate the plasma from the red blood cells. This must be done in a lab that has centrifuge equipment. The plasma must then be quickly tested, as soon as possible after blood processing. In most cases, the blood processing and ammonia level measurement must be carried out in two different areas of the hospital. Thus, a patient must go to a blood-processing lab attached to a hospital to have blood taken for the test. Additionally, the current tests for blood ammonia require an amount of blood that can only be acquired by venipuncture. This makes testing infants and small children additionally challenging.

The most commonly used clinical laboratory test for measuring plasma ammonia utilizes the glutamate dehydrogenase reaction, in which ammonium ion reacts with 2-oxoglutarate and NADPH to form glutamate, NADP and water. Absorbance spectroscopy at 340 nm measures the decrease in NADPH. The assay is highly specific and effective over a broad range of ammonia concentrations. However, the procedure is lengthy and complex, requiring venipuncture for several milliliters of blood, followed by centrifugation for plasma. Samples must be transported on ice to a central laboratory to minimize false elevation of ammonia levels from glutamine deamination in the blood cells. Thus, the standard clinical test is incompatible with close monitoring of patients at risk for hyperammonemia.

One alternative to the standard plasma ammonia analysis is to measure the ammonia concentration in whole blood. To avoid interference from other blood components, this strategy liberates ammonia in gaseous form for separate quantification. Gas-sensing electrodes detect ammonia by release of ammonia by alkalization of the whole blood sample. The electrode is placed above the surface of the sample and protected by a gas permeable membrane. This method has two major disadvantages, however—it requires a large amount of blood to work, and it takes a long time to analyze one sample—10 to 15 minutes at low ammonia levels.

Colorimetric reactions may also be used measure ammonia by spectrometry. Such reactions include the indophenol reaction, which generates a blue color, and the Nessler reaction, which generates a brown-orange color. The disadvantage of such methods is that other substances in the blood, such as amino acids and glutamine, can affect the reactions, leading to inaccuracy.

A more recent colorimetric method for measuring ammonia in whole blood has been developed and incorporated into a device known as the Blood Ammonia Checker or, in a more recent version, the PocketChem Blood Ammonia Analyzer (available from Woodley Equipment Company Ltd.). To measure ammonia, a small drop of blood is placed on a test strip that contains alkaline salts that liberate ammonia from the blood. The ammonia diffuses through a porous separator to a color-developing layer containing bromocresol green. The ammonia is quantified by colorimetry after 3-4 minutes. The problem with this device is that it has been shown to have problems with accuracy. Additionally, sensitivity for detecting elevated ammonia levels is questionable. The dynamic range of a dye-based assay is necessarily limited by the pKa of the dye and the sensitivity of the color detection system. Finally, the price of the Blood Ammonia Analyzer is $3,000.

Therefore, it would be very desirable to have an improved method and device for testing blood ammonia levels. Ideally, such a method and device would be simple to use, relatively inexpensive, and portable. Also ideally, the method and device would be convenient for use in a hospital, physician's office or patient's home. Finally, it would be ideal if such a method and device could be used for one-time blood ammonia level testing, ongoing monitoring of blood ammonia levels, or both. At least some of these objectives will be met by the embodiments described below.

BRIEF SUMMARY

The present disclosure describes a device that uses an electrochemical reaction to detect gaseous ammonia liberated from blood. Various embodiments of the device include a blood sample containment member, an ammonia gas sensor, and a current measurement member coupled with the gas sensor. A small volume blood sample, which in some cases may be as small as a drop of blood (approximately 0.05 mL), is placed in or on the blood sample containment member, which may be a container or substrate. Ammonia liberated out of the blood sample then generates a current in the ammonia gas sensor, which in some embodiments may be an ammonia fuel cell, and this current enters the current measurement member (an electric circuit, for example) Measured current may then be displayed on an ammonia level display. Electrochemical detection should provide more accurate results than the dye-based tests in current use, because it does not share the limited dynamic range of a dye-based assay. Furthermore, miniature ammonia fuel cells, which may be used as the ammonia gas sensor in one embodiment, are inexpensive and readily available. For example, ammonia fuel cells used for industrial safety applications cost approximately $200 each. (One example of a currently available ammonia fuel cell is pictured in FIG. 1.)

Methods described herein typically involve placing a blood sample in or on a sample container or substrate in proximity to an ammonia gas sensor, allowing ammonia liberated from the blood sample to generate a current in the ammonia gas sensor, and measuring the current with a current measurement member coupled with the ammonia gas sensor. The method also typically involves providing a blood ammonia level to a user via a display member coupled with the ammonia gas sensor and/or the current measurement member. In some embodiments, the method may also involve mixing an alkaline substance with the blood sample to facilitate and/or hasten the ammonia leaving the blood. For example, one such substance may be $K_2CO_3$ (potassium carbonate), while another example may be a solution of LiCl/LiOH (Lithium Chloride/Lithium Hydroxide). In some cases, such a solution may be mixed with the blood sample, and the mixture may be stirred or agitated. In other embodiments, the blood sample may simply be placed on a solid support in proximity with the fuel cell, without any further treatment of the sample.

The device embodiments described herein may be very small, portable, inexpensive, and quick to use, thus allowing for blood ammonia testing at a patient's bedside (hospital, nursing home or the like), in a physician's office, at home, or wherever is most convenient to a patient. In some embodiments, for example, the ammonia testing device may be as small and convenient to use as a blood glucose monitoring device commonly used by diabetics. In other embodiments, the device may include additional features, such as capability for transmitting ammonia levels directly to the patient's electronic medical record when tests are performed in the hospital setting. The devices and methods described herein for rapid small volume detection of blood ammonia may provide a significant improvement in detecting and monitoring hyperammonemia. Thus, they may be used to screen millions of patients worldwide to help prevent brain damage and death.

In one aspect, a method for measuring ammonia in a blood sample may involve positioning the blood sample in proximity with an ammonia gas sensor, such as an ammonia fuel cell, and measuring current generated by the fuel cell in response to ammonia released from the blood sample. The method may also involve displaying the measured current on a display coupled with the current measurement member. In some embodiments, positioning the blood sample may involve forming a sealed chamber (or "compartment"), in which the ammonia released from the blood has access to an anode end of the fuel cell. Some embodiments may further include mixing the blood sample with an alkaline substance. For example, in two alternative embodiments, the alkaline substance may be potassium carbonate or an aqueous solution of lithium chloride and lithium hydroxide. Optionally, the method may further include stirring or agitating the blood/alkaline substance mixture.

As mentioned above, in some embodiments, the blood sample may be as small as a drop of blood, or no more than approximately 0.05 mL of blood. In some embodiments, positioning the blood sample may involve contacting a sealed container with the ammonia gas sensor, such that an anode end of the gas sensor is exposed to an open space in the container that contains the blood sample. In other embodiments, positioning the blood sample may involve positioning a substrate holding the blood sample in proximity with an anode end of the ammonia gas sensor, where the anode end and the blood sample are located within a sealed compartment after the positioning step. In some embodiments, an ammeter is used to measure the current generated by the fuel cell.

In another aspect, a method for measuring ammonia in a blood sample may involve positioning the blood sample in proximity with an ammonia fuel cell or other ammonia gas sensor, generating a current with the ammonia fuel cell or other sensor in response to ammonia released from the blood sample, and measuring the current generated by the fuel cell or other sensor.

In another aspect, a device for measuring an ammonia level in a blood sample may include a blood sample containment member, an ammonia gas sensors, such as an ammonia fuel cell, coupled with the blood sample containment member, and a current measurement member coupled with the gas sensor. In some embodiments, the blood sample containment member may be removably attachable to the gas sensor to form a sealed compartment housing an anode end of the fuel cell and the blood sample. In some embodiments, the blood sample containment member comprises a substrate for holding the blood sample. Optionally, such an embodiment may include a substrate that acts as a base to release ammonia, or a substrate treated with substance (for example, a base and/or a salt). The blood sample would then be applied to the substrate.

Typically, the device will be small enough to be easily portable. The device will also be configured to measure blood ammonia levels using only a very small sample of blood, such as no more than a drop of blood, or no more than approximately 0.05 mL of blood. In some embodiments, the ammonia fuel cell may be a miniature ammonia fuel cell, similar to those used in various industrial applications. In some embodiments, the current measurement member may be an ammeter or a potentiostat. In some embodiments, the blood sample containment member may form a chamber in fluid communication with an anode end of the ammonia gas sensor, and the current measurement member may be an electric circuit coupled with the anode end and a cathode end of the ammonia gas sensor.

In some embodiments, the device may further include a housing for containing the blood sample containment member, the ammonia gas sensor and/or the current measurement member. In some embodiments, the device may further include a display on the housing for displaying the measured blood ammonia level. The display may be configured to display the measured blood ammonia level numerically, as a linear display (such as a graph), and/or via any other suitable representation, according to various embodiments.

These and other aspects and embodiments will be described in further detail below, in reference to the attached drawing figures.

DETAILED DESCRIPTION

The following description is directed to embodiments of a device and method for measuring ammonia levels in a blood sample. The embodiments provided below are meant to be exemplary in nature and should not be interpreted as limiting the scope of the invention. For example, in various alternative embodiments, it may be possible to eliminate or alter one or more device features, eliminate or alter one or more method steps, change the order of method steps, and/or the like. As one specific example, although the following description focuses on the use of the device and method embodiments for detecting ammonia levels in blood samples, in alternative embodiments, these same embodiments or variations thereof may be used to detect ammonia levels in other substances.

Figure 1:
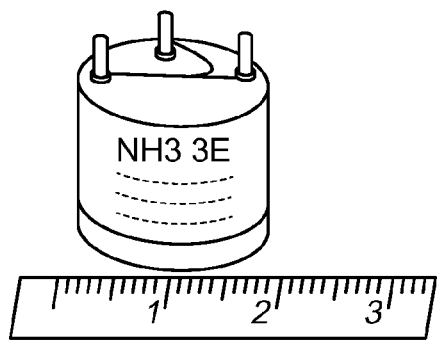
FIG. 1 is a perspective view of an industrial ammonia fuel cell.
Figure 2:
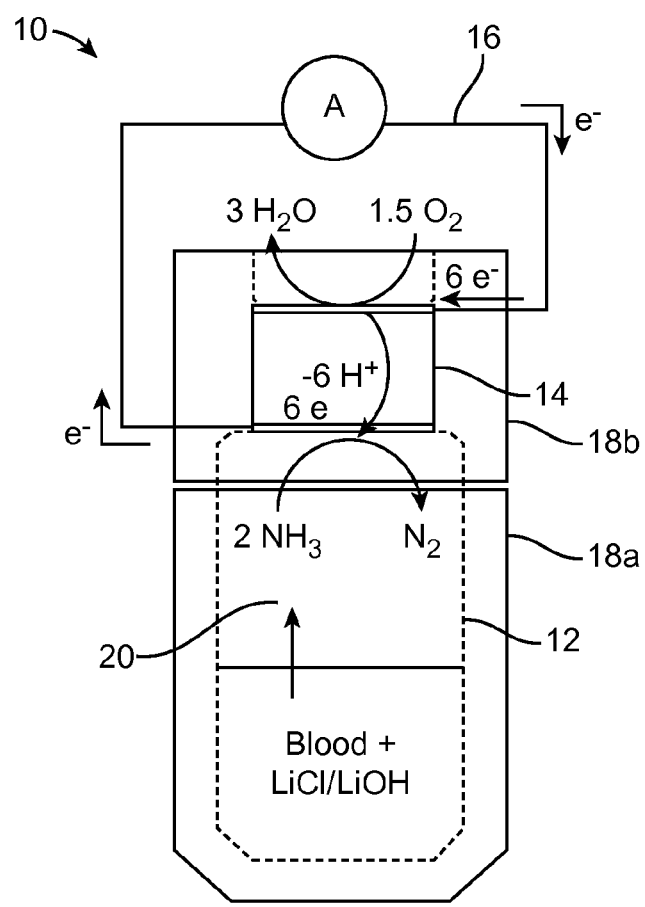
FIG. 2 is a diagrammatic representation of a blood ammonia level measurement device, according to one embodiment.

Referring now to FIG. 2, in one embodiment, a rapid, small volume, blood ammonia detection device 10 includes a blood sample containment member 12 coupled with an ammonia (NH3) fuel cell 14, which is coupled with a current measurement member 16. In various alternative embodiments, fuel cell 14 may be replaced by any other suitable ammonia gas sensor, such as but not limited to a redox mediator. Therefore, although the embodiment illustrated in FIG. 2 and much of the following description discusses a "fuel cell," alternative embodiments may include any suitable substitute ammonia gas sensor. Therefore, this application should not be interpreted as being limited to only embodiments including fuel cells.

Similarly, in one embodiment, as shown in FIG. 2, blood sample containment member 12 may be a container for holding a blood sample. One example of blood containment member 12 may be a vial with a cap and a membrane. In this embodiment, a blood sample may be placed in the vial, and the cap and membrane may seal containment member 12. When containment member 12 is then attached to fuel cell 14 and/or a housing containing fuel cell 14, the membrane may be pierced, thus forming a chamber that is exposed to fuel cell 14 but is still sealed. In alternative embodiments, blood sample containment member 12 may be a substrate, such as a plate, slide, piece of flat material or the like. In substrate embodiments, blood sample containment member 12 may be positioned in proximity to fuel cell 14 for measurement of the ammonia gas. In the embodiment shown, current measurement member 16 is a potentiostat. In alternative embodiments, current measurement member 16 may be an ammeter or other type of circuit or other current measurement device.

Containment member 12, fuel cell 14 and current measurement member 16 may be entirely or partially contained in a housing 18a, 18b. In the diagrammatic representation of FIG. 2, housing 18a, 18b is depicted as having a blood sample portion 18a and a fuel cell portion 18b, which may fit together to form a seal, thus sealing in the blood sample within an airtight chamber. (Alternatively, blood sample portion 18a may simply be blood containment member 12—in other words, such an embodiment would not have a separate blood sample housing portion 18a.) In this configuration, openings in containment member 12 and blood sample portion 18a allow an anode end (or "anode side") of fuel cell 14 to have access to what is referred to herein as a headspace 20—the space directly above the blood sample and in air contact with the anode end of fuel cell 14. Otherwise, the blood sample and anode end are sealed off from outside air. As illustrated in FIG. 2, in some embodiments, current measurement member 16 may extend out of fuel cell portion 18b of the housing. In an alternative embodiment, containment member 12, fuel cell 14 and current measurement member 16 may all be housed within housing 18a, 18b. In another alternative embodiment, the housing may be a one-piece structure, and blood sample containment member 12 may be inserted into it once a blood sample is loaded, or a blood sample itself may be inserted into device 10 through an opening. Optionally, a display on an outside of housing 18a, 18b (not shown) may display a measured ammonia level. In some embodiments, such as the one depicted diagrammatically in FIG. 2, containment member 12 may actually be its own housing 18a.

In various embodiments, containment member 12 may have any suitable size, shape and configuration and may be made of any suitable material. For example, containment member 12 may be a cuplike container, with a means for sealing the open end of the cup to fuel cell 14. Alternatively, containment member 12 may be a vial with a sealed or sealable cap. A blood sample may be inserted into the vial or cup, and in one embodiment device 10 may include a puncturing element that punctures one or more holes in a cap of the containment member 12 when it is attached to device 10, thus allowing liberated blood ammonia to contact fuel cell 14. In some embodiments, containment member 12 may be extremely small, since it typically only needs to hold one drop or 50 microliters of blood. As described further below, for example, in some embodiments containment member 12 may simply be a flat substrate.

Fuel cell 14 may be any currently available or not-yet-invented ammonia fuel cell, such as but not limited to currently available, small, lightweight ammonia fuel cells that are worn as badges by industrial workers at risk for ammonia exposure. As mentioned above, in other alternative embodiments, fuel cell 14 may be replaced by an alternative type of ammonia gas sensor. Fuel cell 14 may include three electrodes, one of which attaches to an anode of current measurement member 16, one of which attaches to a cathode of current measurement member 16, and one of which attaches to a reference electrode. In one embodiment, all three of these attachments are wired attachments. Other electrode configurations may be possible in alternative embodiments. For example, it may be possible to eliminate or substitute some other configuration for the reference electrode.

Device 10 is configured to detect gaseous NH3 liberated from a blood sample and exposed to fuel cell 14 in headspace 20, thus generating a current response proportional to the NH3 concentration in the sample. During operation, sample containment member 12 is sealed to the anode side of fuel cell 14. The blood sample is injected into containment member 12 and subsequently treated with an alkaline substance, such as but not limited to potassium carbonate, LiCl/LiOH, other hydroxides, and other salts. The increase in the pH and ionic strength of the blood when mixed with a substance like potassium carbonate or LiCl/LiOH causes the release of NH3 into headspace 20. NH3 oxidation at the anode end of fuel cell 14, coupled with oxygen (O2) reduction at the cathode end of fuel cell 14, generates a current that is measured by current measurement member 16. Since release of NH3 into headspace 20 is faster than its consumption at the anode, NH3 effectively equilibrates between headspace 20 and the blood sample. The current rises to a plateau value that is proportional to this steady state headspace concentration, and therefore proportional to the sample concentration. The response is taken as the peak current, which provides an accurate measurement of blood ammonia level.

The amount of blood used for the sample may be very small. For example, in some embodiments, one drop of blood may be used—e.g., no more than approximately 0.05 mL (50 microliters) of blood. This is in contrast to currently available blood ammonia measurement techniques, which typically require at least 3000-10,000 microliters of blood. In various embodiments, any suitable alkaline solution may be mixed with the blood, or in other alternative embodiments, blood may be measured without mixing with an alkaline solution. In one embodiment, it was found to be advantageous to elevate the pH of the blood sample to approximately 11, using LiOH, while at the same time increasing the ionic strength of the blood sample using LiCl. In an alternative embodiment, it was found to be advantageous to use potassium carbonate (K2CO3). In general, carbonates, such as potassium carbonate, may be preferable to hydroxides for safety reasons.

In some embodiments, the blood sample may be injected, or otherwise delivered into containment member 12. In alternative embodiments, it may be possible to simply apply a drop of blood to a solid substrate, such as a flat piece of glass, glass fibers, paper or other material. The flat substrate may be placed immediately below the anode end of fuel cell 14. In various alternative embodiments, the substrate may be either untreated or pretreated with a substance, such as a salt and/or base. In some embodiments, device 10 may include a finger stick component, such that a patient may prick his or her finger, a drop of blood from the finger deposits on the sample substrate, and device 10 detects the blood ammonia level. Detection of the ammonia level in the blood sample by device 10 may in some embodiments occur very quickly, for example in a few minutes or even just a few seconds.

Device 10 may provide the measurement of the blood ammonia level in a number of different ways in different embodiments. For example, in some embodiments, device 10 may include a built-in, digital, numerical display, which shows a measured ammonia level. In such an embodiment, device 10 may optionally beep, flash or otherwise signal when the equilibrium ammonia level is reached, analogous to digital thermometers that signal to a user when the body temperature is measured. In other embodiments, device 10 may store and/or transmit blood ammonia measurement for display on another device, such as a laptop or desktop computer. For example, device 10 may have Bluetooth capabilities or may plug into a computer via a USB port.

In some embodiments, device 10 may be entirely disposable, while in alternative embodiments, some or all of device may be reusable. For example, in some embodiments, containment member 12 may be disposable while the remainder of device 10 is reusable. In other embodiments, all of device 10 may be reusable, and a blood sample carrying substrate may be placed into containment member 12, such that the substrate is disposed of after use and the container is reused.

Experimental Measurement of NH3 in Whole Blood

Experiment #1

Figure 3:
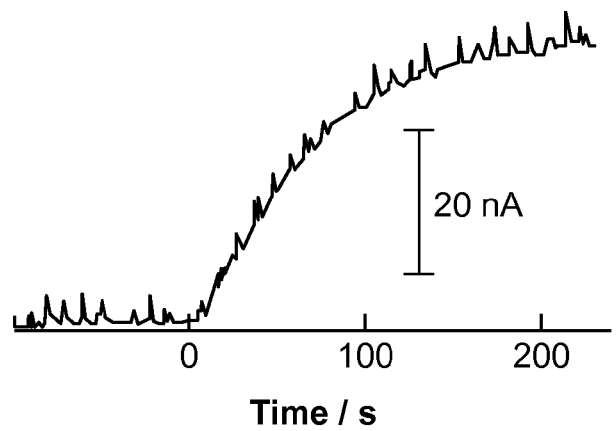
FIG. 3 is a graph showing time on the horizontal axis and current on the vertical axis, illustrating a current vs. time response to ammonia release from blood, according to one embodiment and one sample.

An initial set of experiments was performed to optimize the release of NH3 from blood and determine whether device 10 responds linearly to NH3 content in blood. (Anonymous whole blood samples were obtained from the Stanford Blood Bank according to their human subjects protocol.) Rapid responses were obtained by injecting 300 μL of whole blood into sample containment member 12, followed by 180 μL of an aqueous solution containing 0.2 M LiOH and 12 M LiCl ("LiOH/LiCl"). The blood and reagents were mixed with a magnetic stir bar while the current response from the detector was recorded. FIG. 3 shows one example of a typical current vs. time trace for this experiment. Device 10 reached a quasi-steady state current within 3 minutes of the addition of LiOH/LiCl. Unless otherwise noted, this optimized procedure was used for all whole blood analyses discussed below.

Experiment #2

Figure 4:
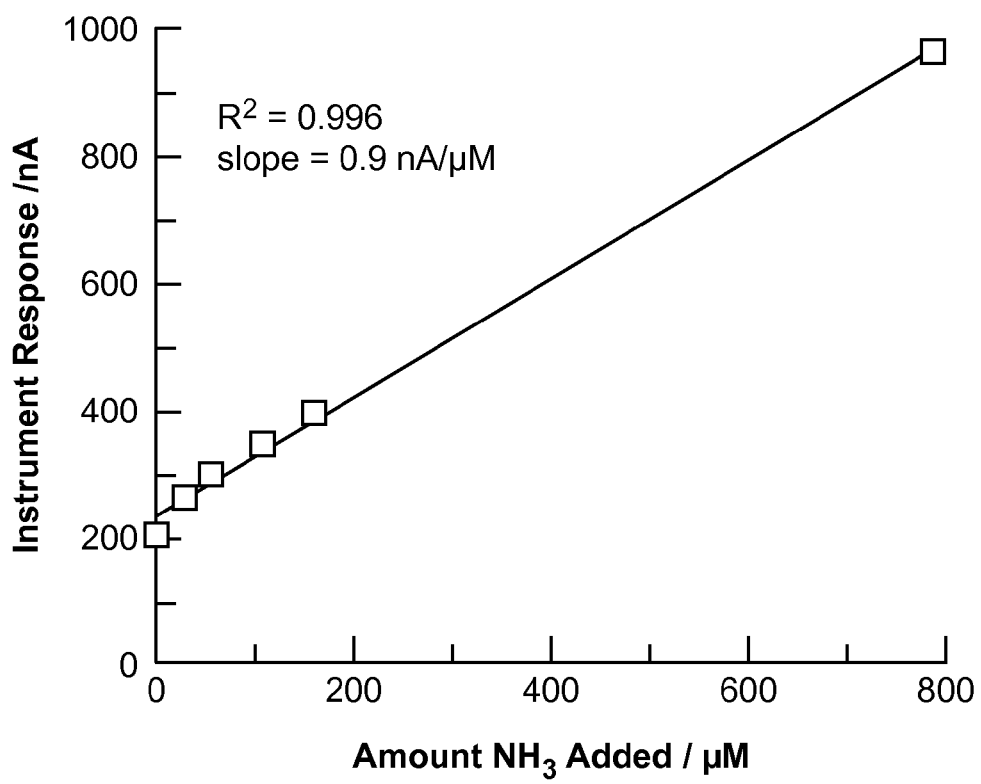
FIG. 4 is a graph illustrating a standard curve measurement of ammonia in whole blood, using devices and methods according to one embodiment.

A set of blood samples spanning a range of NH3 concentrations was prepared by dividing blood from a single donor into 5 aliquots and adding a different amount of NH3 in the form of NH4Cl to each aliquot. The amount of NH3 added ranged from 0 to 800 μM. FIG. 4 shows the response of the instrument as a function of the amount of added NH3. A smooth linear response was obtained across the 5 samples with a slope of 1 nA/μM NH3. As expected, an appreciable response was obtained for the sample with no added NH3, which reflected the amount of NH3 naturally present in the sample. This experiment demonstrated the ability of device 10 to detect NH3 directly from whole blood and quantify the difference in NH3 content between samples.

Experiment #3

Figure 5:
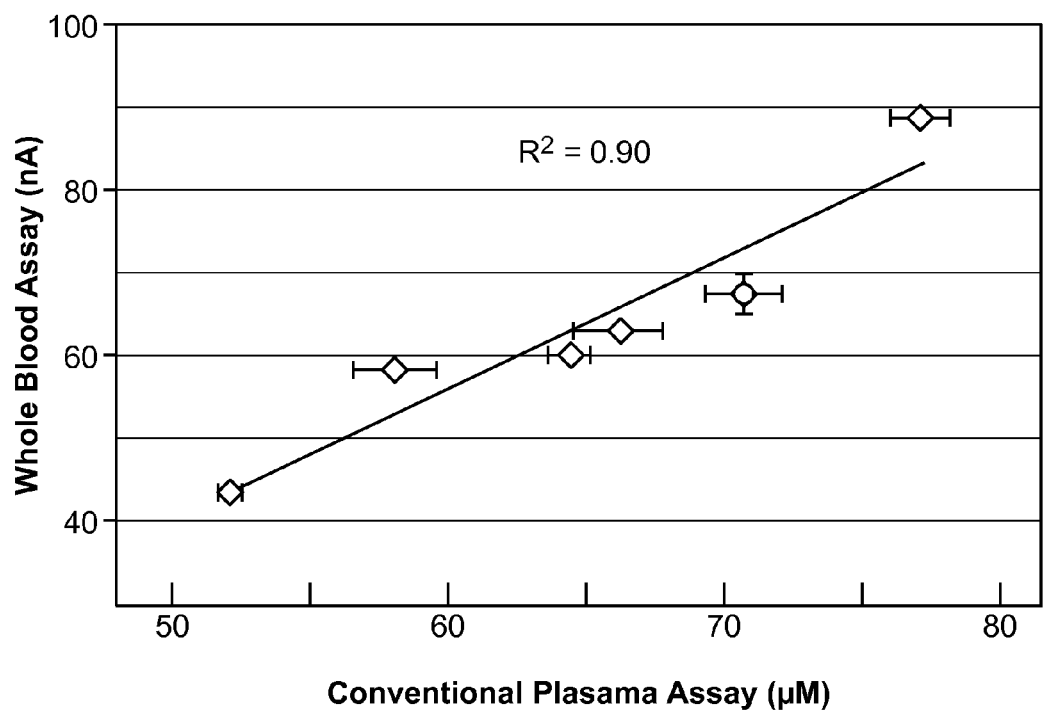
FIG. 5 is graph illustrating a conventional plasma assay vs. a whole blood ammonia level detection technique, according to one embodiment.

Ideally, whole blood analysis of ammonia levels, using the devices and methods described herein, will strongly correlate with NH3 measured for plasma. To address this question, response of device 10 to the NH3 released from whole blood samples was compared to the NH3 concentration in the plasma of the same samples measured by the conventional enzymatic analysis. Fresh 10 mL whole blood samples were obtained from 5 healthy donors at the Stanford Blood Center and transported on ice to the lab. The samples were analyzed in series to minimize the time between whole blood and plasma analysis for each individual sample. An aliquot was removed from the first sample and kept on ice, while the remainder of the sample was centrifuged to separate the plasma. During centrifugation, the whole blood aliquot was analyzed in duplicate with the instrument. The plasma that had been separated was then assayed in triplicate using the conventional enzymatic assay. This procedure was repeated for the 4 remaining whole blood samples. FIG. 5 shows a plot of the instrument response to the whole blood aliquots vs. the NH3 concentration in the corresponding plasma. A good linear fit (R2=0.90) was obtained for the six samples, which had measured plasma NH3 levels ranging from 52 µM to 77 µM. Furthermore, device 10 response was less noisy than the conventional enzyme-based plasma assay. Thus, the data suggest that device 10 is potentially much more reliable than both the conventional enzyme-based plasma assay and the dye-based Blood Ammonia Checker.

Measurement of NH3 from a Drop of Blood Spotted onto a Solid Support

Especially for home detection of blood ammonia, it would be ideal to require only the smallest possible blood sample volume and to make the analysis procedure as simple as possible. Ideally, the analysis could be performed with a drop (20-50 µL) of blood on a solid support. In some cases, the support may be preloaded with salt and/or base that would facilitate release of NH3 from the blood sample as it dries. A preliminary experiment to assess the feasibility of this approach was performed.

A fresh whole blood sample was divided into two aliquots, and 167 µM of NH4Cl was added to one aliquot. Glass microfiber discs were soaked with either KCl solution or KCl solution+LiOH/LiCl, then rinsed with H2O and dried. The disc was placed into sample-mixing containment member 12 of device 10. A 50 µL drop of blood was added to the disc, and sample containment member 12 was immediately sealed to fuel cell 14. Table 1 shows the current response for blood drops with and without added NH4Cl, using the two methods for pre-treating the glass fiber filter, either with KCl alone or KCl plus LiOH.

TABLE 1

Whole blood spotted onto a solid support

| Blood sample | Microfiber filter treatment | Response (nA) |
|---|---|---|
| None | Soaked with KCl solution, dried | 11 |
| Native sample | Soaked with KCl solution, dried | 28 |
| +167 µM NH4Cl | Soaked with KCl solution, dried | 44 |
| Native sample | Soaked with KCl + LiOH/LiCl solution, dried | 22 |
| +167 µM NH4Cl | Soaked with KCl + LiOH/LiCl solution, dried | 46 |

Blood without added NH4Cl produced a response significantly above the baseline current, indicative of the ammonia level in the blood sample. Blood with added NH4Cl produced an approximately 2-fold higher response, with an incremental increase of about 20 nA. The results suggest that the glass fiber filter itself may be effectively alkalinizing the blood sample to release ammonia, thus eliminating the need for treating the filter with base. Most importantly, this preliminary experiment indicates that electrochemical detection of NH3 released from a drop of blood on a solid support is feasible. By using a small sample container/substrate 12 to match the small sample size, it may be possible to provide both an increase in the response current and also a substantial decrease in the time to reach a current plateau. These improvements may make it possible to accurately quantify whole blood ammonia from a single drop of blood within seconds.

Although various embodiments and examples are described above, these embodiments and examples should not be interpreted as limiting the scope of the present invention. Any of a number of suitable modifications may be made to any of the above-described embodiments, without departing from the scope. Thus, the embodiments are meant to be exemplary in nature and not limiting.

What is claimed is:

1. A method for measuring ammonia in a blood sample, the method comprising:
   positioning the blood sample in proximity with an ammonia gas sensor;
   mixing the blood sample with an alkaline substance;
   generating a current with the ammonia gas sensor in response to ammonia gas released from the blood sample; and
   measuring the current generated by the ammonia gas sensor, using a current measurement member coupled with the ammonia gas sensor.

2. A method as in claim 1, wherein the ammonia gas sensor comprises an ammonia fuel cell, and wherein positioning the blood sample comprises positioning the blood sample in a sealed chamber that surrounds at least part of an anode end of the ammonia fuel cell so that the anode end is exposed to the ammonia gas released from the blood sample.

3. A method as in claim 2, wherein positioning the blood sample further comprises attaching the blood sample containment member to the ammonia fuel cell to form the sealed chamber.

4. A method as in claim 3, wherein attaching the blood sample containment member to the ammonia fuel cell forms at least one aperture in the blood sample containment member to form the sealed chamber.

5. A method as in claim 1, wherein the blood sample comprises no more than about 0.05 mL of blood.

6. A method as in claim 1, wherein mixing the blood sample is performed before positioning the blood sample.

7. A method as in claim 1, wherein mixing the blood sample is performed after positioning the blood sample.

8. A method as in claim 1, wherein the alkaline substance is selected from the group consisting of: potassium carbonate; an aqueous solution of lithium chloride and lithium hydroxide; other hydroxides; and other salts.

9. A method as in claim 1, further comprising stirring or agitating the blood sample and the alkaline substance at least one of during or after the mixing step.

10. A method as in claim 1, wherein positioning the blood sample comprises positioning a substrate holding the blood sample in proximity with an anode end of the ammonia gas sensor.

11. A method as in claim 1, wherein measuring the current comprises measuring with an ammeter.

12. A method as in claim 1, wherein measuring the current comprises measuring with a potentiostat.

13. A method as in claim 1, further comprising displaying the measured current on a display member coupled with the current measurement member.

14. A method as in claim 1, wherein the method is performed using a portable ammonia measurement device comprising a blood sample containment member, an ammonia gas sensor coupled with the blood sample containment member, and a current measurement member coupled with the ammonia gas sensor, and wherein the portable ammonia measurement device is configured to be held in one hand of a user.

15. A device for measuring an ammonia level in a blood sample, the device comprising:
    a blood sample containment member;
    an ammonia gas sensor comprising an ammonia fuel cell coupled with the blood sample containment member; and
    a current measurement member coupled with the ammonia gas sensor.

16. A device as in claim 15, wherein the blood sample containment member is removably coupled with the ammonia gas sensor.

17. A device as in claim 15, wherein the blood sample containment member comprises a compartment for holding the blood sample, wherein the compartment forms a sealed chamber when the blood sample containment member is coupled with the ammonia gas sensor, and wherein the sealed chamber encloses an anode end of the ammonia gas sensor and the blood sample.

18. A device as in claim 17, wherein the current measurement member comprises an electric circuit coupled at one end with the anode end of the ammonia gas sensor and at an another end with a cathode end of the ammonia gas sensor.

19. A device as in claim 15, wherein the blood sample containment member comprises a substrate for holding the blood sample.

20. A device as in claim 19, further comprising a substance pre-applied onto the substrate before application of the blood sample to the substrate.

21. A device as in claim 20, wherein the substance is selected from the group consisting of: potassium carbonate; an aqueous solution of lithium chloride and lithium hydroxide; other hydroxides; and other salts.

22. A device as in claim 15, wherein the current measurement member comprises an ammeter.

23. A device as in claim 15, wherein the current measurement member comprises a potentiostat.

24. A device as in claim 15, further comprising a housing at least partially containing the ammonia gas sensor and the current measurement member, wherein the blood sample containment member is removably couplable with the housing.

25. A device as in claim 24, wherein the blood sample containment member comprises a container couplable with the housing to form a sealed chamber in which the blood sample is contained.

26. A device as in claim 25, wherein the blood sample containment member comprises a sealed vial comprising a membrane, and wherein coupling the blood sample containment member with the housing pierces the membrane and forms the sealed chamber.

27. A device as in claim 24, wherein the blood containment member comprises a substrate, and wherein the housing comprises a slot into which the substrate is advanced to expose the blood sample to the ammonia gas sensor.

28. A device as in claim 24, further comprising a display on the housing for displaying the measured blood ammonia level.

29. A device as in claim 28, wherein the display is configured to display at least one of a numerical indication or a linear representation of the measured blood ammonia level.

30. A device as in claim 15, further comprising a two-part housing, wherein a first part of the two-part housing at least partially contains the ammonia gas sensor and the current measurement member, and wherein a second part of the two-part housing at least partially contains the blood sample containment member.

31. A device as in claim 15, wherein the device is configured to measure the ammonia level in the blood sample, wherein the blood sample comprises no more than about 0.05 mL of blood.

32. A device as in claim 15, wherein the device is sufficiently small to be held in one hand of a user while in use.

* * * * *